United States Patent [19]

Annen et al.

[11] Patent Number: 4,555,507

[45] Date of Patent: Nov. 26, 1985

[54] NOVEL 6, 16-DIMETHYLCORTICOIDS, THEIR PREPARATION AND USE

[75] Inventors: Klaus Annen; Henry Laurent; Helmut Hofmeister; Rudolf Wiechert; Michael Töepert; Hans Wendt, all of Berlin, Fed. Rep. of Germany

[73] Assignee: Schering Aktiengesellschaft, Berlin, Fed. Rep. of Germany

[21] Appl. No.: 515,243

[22] Filed: Jul. 19, 1983

[30] Foreign Application Priority Data

Jul. 19, 1982 [DE] Fed. Rep. of Germany ....... 3227312

[51] Int. Cl.$^4$ ............................................. C07J 5/00
[52] U.S. Cl. ............................. 514/172; 260/397.45; 260/239.55 R
[58] Field of Search .................... 260/397.45; 314/172

[56] References Cited

U.S. PATENT DOCUMENTS 3,054,811  9/1962  Arth et al. ..................... 260/397.45
3,152,154 10/1964  Ercoli et al. ..................... 424/243
3,312,590  4/1967  Elks et al. ........................ 424/243
4,154,748  5/1979  Van Rheenen et al. ......... 260/397.4

FOREIGN PATENT DOCUMENTS 898291  6/1962  United Kingdom ........... 260/397.45
898292  6/1962  United Kingdom ........... 260/397.45
1544642  9/1962  United Kingdom ........... 260/397.45
931221  7/1963  United Kingdom ........... 260/397.45
1047519 11/1966  United Kingdom ........... 260/397.45

OTHER PUBLICATIONS

Synthesis 1982, Nr. 1, Jan. 1982, Georg Thieme Verlag Stuttgart-New York, US, Klaus Annen et al.: "A Simple Method for 6-Methylenation of 3-Oxo-$\Delta^4$-steroids", Seiten 34–40.

European Search Report EP 83 10 6649, dated Nov. 19, 1984.

Sugai et al., "Synthesis 1982 (12) pp. 102 3-5, as abstracted in Chem. Abstracts vol. 98(1983) Par. 143712t.

Primary Examiner—Elbert L. Roberts
Attorney, Agent, or Firm—Millen & White

[57] ABSTRACT

Compounds of Formula I

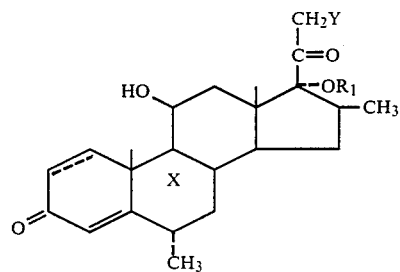

wherein
the bond ===== is a single bond or a double bond,
X is hydrogen, flourine, chlorine, or bromine,
$R_1$ is formyl, alkanoyl or alkoxyalkyl each of which contains 2–8 carbon atoms, or benzoyl, and
Y is chlorine, hydroxy, formyl, alkanoyloxy of 2–8 carbon atoms, or benzoyloxy, have valuable anti-inflammatory properties.

16 Claims, No Drawings

NOVEL 6, 16-DIMETHYLCORTICOIDS, THEIR PREPARATION AND USE

BACKGROUND OF THE INVENTION

The present invention relates to new 6,16-dimethylcorticoids, to pharmaceutical preparations containing them, to a process for the preparation of these compounds; and to intermediate steroidal products used in the synthesis of these compounds.

SUMMARY OF THE INVENTION

It is an object of this invention to provide new steroids having valuable pharmacological properties.

Upon further study of the specification and appended claims, further objects and advantages of this invention will become apparent to those skilled in the art.

These objects have been achieved by providing 6,16-dimethylcorticoids of Formula I

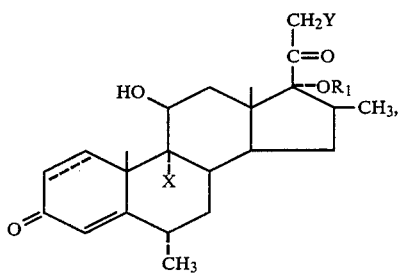

wherein
the bond $=\!=\!=\!=\!=$ is a single bond or a double bond,
X is hydrogen, flourine, chlorine, or bromine,
$R_1$ is formyl, alkanoyl or alkoxyalkyl, each of which contains 2-8 carbon atoms, or benzoyl, and
Y is chlorine, hydroxy, formyl, alkanoyloxy of 2-8 carbon atoms, or benzoyloxy.

DETAILED DISCUSSION

The novel 6,16-dimethylcorticoids of this invention can contain as $R_1$, a formyl group, an alkanoyl group or alkoxyalkyl group containing 2-8 (preferably 2-6) carbon atoms, or a benzoyl group. Suitable alkanoyl groups $R_1$ include, for example, acetyl, propionyl, butyryl, isobutyryl, valeryl, 3-methylbutyryl, trimethylacetyl, or hexanoyl. Especially suitable examples of alkoxyalkyl groups $R_2$ include alkoxymethyl groups, such as methoxymethyl, ethoxymethyl, propoxymethyl, isopropoxymethyl, butoxymethyl, isobutoxymethyl, or tert-butoxymethyl.

The 6,16-dimethylcorticoids can contain as Y a chlorine atom, a hydroxy group, an alkanoyloxy group containing 2-8 (preferably 2-6) carbon atoms, or a benzoyloxy group. Suitable alkanoyloxy groups include, for example, those derived from the above-mentioned alkanoyl groups.

The 6,16-dimethylcorticoids of Formula I are distinguished by an excellent anti-inflammatory activity in mammals, including humans, e.g., upon topical application. Moreover, they are distinguished by an excellent dissociation between desirable topical efficacy and undesirable systemic side effects.

It is to be noted that the 6,16-dimethylcorticoids of Formula I wherein X is hydrogen, flourine, or chlorine are more suited for use in pharmaceutical preparations than are those wherein X is bromine, since the latter are less stable in galenic preparations. However, on the other hand, in addition to their inherent utility as mentioned, the 9-bromo-steroids of Formula I are valuable intermediates for the synthesis of the other, pharmacologically effective 6,16-dimethylcorticoids of the present invention using fully conventional preparative methods.

Hence, the novel 6,16-dimethylcorticoids of Formula I are suitable, in combination with the excipients customary in galenic pharmacy, for the local treatment of contact dermatitis, eczemas of a great variety of types, neurodermatoses, erythrodermia, burns, pruritus vulvae et ani, rosacea, erythematodes cutaneus, psoriasis, lichen ruber planus et verrucosus, and similar diseases of the skin.

The drug specialties can be prepared in the usual way, by bringing the active agents and suitable additives into the desired form of administration, such as, for example: solutions, lotions, ointments, creams, or plasters. In the thus-formulated medicinal agents, the active agent concentration is dependent on the form of administration. In the case of lotions and ointments, an active agent concentration of 0.001% to 1% is preferably employed. Administration is fully conventional as with such topical formulations, e.g., those based on hydrocortisone.

Moreover, the compounds of this invention optionally combined with the usual excipients and auxiliary agents, are also well suited for the preparation of inhalants which can be utilized for therapy of allergic diseases of the respiratory tract, such as, for example, bronchial asthma or rhinitis. These can be administered analogously to the administration of the conventional inhalant beclomethasone dipropionate.

The novel corticoids are furthermore also suitable for the treatment of allergic diseases of the intestinal tract, such as colitis ulcerosa and colitis granulomatosa, in the form of capsules, tablets, or dragees containing preferably 10-200 mg of active agent and administered orally, e.g., at daily dosages of 0.2-20 mg/kg, or in the form of suspensions containing preferably 100-500 mg of active ingredient per dosage unit and administered rectally, e.g., at daily dosages of 0.2-20 mg/kg, all analogously to the administration of the conventional anti-inflammatory betamethasone disodium phosphate.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositons can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol.

The novel 6,16-dimethylcorticoids can be prepared according to conventional processes conducted under fully conventional conditions, e.g., those disclosed in German patent application Nos. P 26 45 105.8 (GB No. 1,594,852) and P 28 93 661.5 (U.S. Pat. No. 4,207,316) whose disclosures are incorporated by reference herein. Thus, using these fully conventional processes, the compounds of formula I can be prepared from the corresponding known 17,21-dihydroxy-compounds.

Moreover, additional known processes for the preparation of 6,16-dimethylcorticoids of Formula I comprise conventionally, (a) opening the epoxy ring of a steroid of Formula II

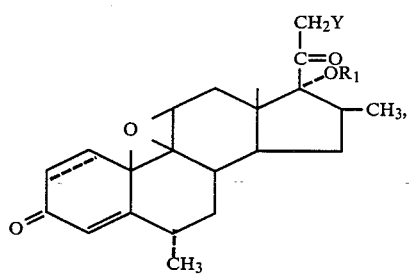

wherein ------, $R_1$, and Y are as defined above, with hydrogen flouride; or (b) chemically adding hypochlorous or hypobromous acid to the $\Delta^{9(11)}$-double bond of a steroid of Formula III

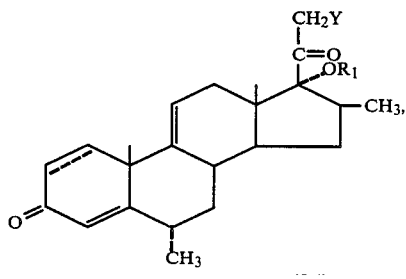

wherein ------, $R_1$, and Y are as defined above, and, optionally, eliminating the 9-positioned halogen atom from the 9-chloro- or 9-bromo-steroids of Formula I; saponifying 21-acetoxy steroids of Formula I and/or esterifying 21-hydroxy steroids of Formula I;

The intermediates of formula IV

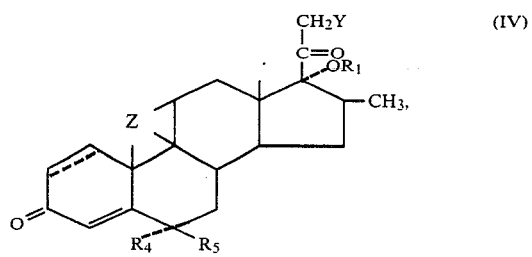

wherein

------, $R_1$, and Y are as defined for formula I,

Z is a carbon-carbon bond or an oxygen atom, and wherein $R_4$ and $R_5$ jointly represent a methylene group, or $R_4$ is a hydrogen atom or a methyl group and $R_5$ is a hydrogen atom are novel. All can be prepared using fully conventional procedures from starting materials which are known and/or fully conventionally preparable.

For example, the compounds of Formula III, but without the 6-methyl group and with a 17-OH and a 21-OH group, can be converted into compounds of Formula III without the 6-methyl group under the conditions of BP No. 1,594,852 or U.S. Pat. No. 4,207,316 and a 6-methyl group can be added in the 6-position under the conditions described in U.S. Pat. No. 4,322,349. The compounds thus obtained can fully conventionally be: dehydrogenated and/or hydrogenated in the $\Delta^{1,2}$-position to form the corresponding 6α-methyl compounds, and/or converted to the corresponding 9,11-epoxide. See, e.g., U.S. Pat. Nos. 3,678,034, 3,718,671, 4,207,316 and 4,322,349. All the references mentioned above are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(A) By way of a water trap, 720 ml of benzene is distilled off at 130° C. from a solution of 24.0 g of 17α,21-dihydroxy-16β-methyl-4,9(11)-pregnadiene-3,20-dione and 2.4 g of pyridinium tosylate in 180 ml of dimethylformamide and 1.7 l of benzene. Into the hot solution, 58 ml of the triethylester of orthopropionic acid is gradually added, and then benzene and other readily volatile reaction components are furthermore removed by distillation. Then 29 ml of pyridine is added, and the mixture is concentrated to dryness under vacuum, thus isolating 17α,21-(1-ethoxypropylidenedioxy)-16β-methyl-4,9(11)-pregnadiene-3,20-dione as an oil.

(B) The crude 17α,21-(1-ethoxypropylidenedioxy)-16β-methyl-4,9(11)-pregnadiene-3,20-dione is dissolved in 720 ml of methanol and stirred with a mixture of 258 ml of 0.1N aqueous acetic acid and 28.8 ml of 0.1-molar aqueous sodium acetate solution for 1.5 hours at a bath temperature of 100° C. The solution is concentrated to ⅓ its volume, poured on water, and the ethyl acetate extracts are washed neutral. After drying and concentration, the crude product is purified on 2 kg of silica gel with a methylene chlorideacetone gradient (0–15% acetone), thus obtaining 23.7 g of 21-hydroxy-16β-methyl-17α-propionyloxy-4,9(11)-pregnadiene-3,20-dione, mp 192° C.

(C) 7.9 g of 21-hydroxy-16β-methyl-17α-propionyloxy-4,9(11)-pregnadiene-3,20-dione is stirred in 79 ml of pyridine and 39 ml of acetic anhydride for one hour at room temperature. After precipitation into ice water and working the mixture up as usual, 8.15 g of 21-acetoxy-16β-methyl-17α-propionyloxy-4,9(11)-pregnadiene-3,20-dione is isolated, mp 95°–96° C.

(D) A suspension of 10.0 g of sodium acetate in 300 ml of chloroform and 300 ml of formaldehyde dimethylacetal is agitated with 19 ml of phosphorus oxychloride for one hour at 65° C. bath temperature. After adding 10.0 g of 21-acetoxy-16β-methyl-17α-propionyloxy-4,9(11)-pregnadiene-3,20-dione, another 19 ml of phosphorus oxychloride is added dropwise to the reaction mixture and the latter is further agitated for 6.5 hours at 65° C. The cooled reaction solution is treated with such an amount of a saturated soda solution that the aqueous phase remains alkaline. The organic phase is separated, washed neutral, and concentrated after drying. The crude product is purified on 700 g of silica gel with a hexane-ethyl acetate gradient (0–50% ethyl acetate), thus isolating 7.5 g of 21-acetox-16β-methyl-6-methylene-17α-propionyloxy-4,9(11)-pregnadiene-3,20-dione, mp 206°–207° C.

. (E) 7.0 g of 21-acetoxy-16β-methyl-6-methylene-17α-propionyloxy-4,9(11)-pregnadiene-3,20-dione and 1.4 g of palladium/active carbon (9.64% strength) are suspended in 350 ml of isopropanol and stirred with 21 ml of cyclohexene for 5 hours at a bath temperature of 120° C. After cooling, the catalyst is removed by vacuum-filtering, washed with methylene chloride, and the combined filtrates are agitated with 40 ml of concentrated hydrochloric acid for 0.5 hour at room temperature. The reaction solution is concentrated to ⅓ of its volume, poured on ice water, and worked up as usual. The crude product is purified on 600 g of silica gel with a hexane-ethyl acetate gradient (0–50% ethyl acetate). Yield: 5.4 g of 21-acetoxy-6α,16β-dimethyl-17α-propionyloxy-4,9(11)-pregnadiene-3,20-dione, mp 184°–185° C.

(F) A suspension of 4.4 g of 21-acetoxy-6α,16β-dimethyl-17α-propionyloxy-4,9(11)-pregnadiene-3,20-dione in 68 ml of dioxane and 4.4 ml of water is combined in portions with 3.3 g of N-bromosuccinimide at an internal temperature of 20° C. During the dropwise addition of a solution of 0.35 ml of 70% perchloric acid in 5.3 ml of water, the internal temperature must not exceed 23° C. The mixture is stirred for 45 minutes at an internal temperature of 20° C., then cooled to +15° C., and neutralized by the dropwise addition of a solution of 1.6 g of sodium acetate and 1.0 g of sodium sulfite in 9.7 ml of water. During this step, the internal temperature must not rise beyond 23° C. After the addition of 60 ml of methanol, the reaction mixture is further stirred for 15 minutes at room temperature and, after adding 172 ml of water, for 3 hours at 0° C. Finally, the precipitate is suctioned off, the residue is washed neutral with water and dried at 70° C. in a vacuum drying cabinet. The crude product is purified on 350.0 g of silica gel with a methylene chloride-acetone gradient (0–8% acetone), thus obtaining 3.2 g of 21-acetoxy-9α-bromo-11β-hydroxy-6α,16β-dimethyl-17α-propionyloxy-4-pregnene-3,20-dione, mp 176°–178° C.

(G) A suspension is prepared from 600 mg of 21-acetoxy-9α-bromo-11β-hydroxy-6α,16β-dimethyl-17α-propionyloxy-4-pregnene-3,20-dione in 12.5 ml of anhydrous tetrahydrofuran and refluxed, after adding 0.63 ml of tributyltin hydride and 20 mg of azobisisobutyronitrile, for 0.5 hour. The mixture is concentrated under vacuum and the residue purified on 100 g of silica gel with a hexane-ethyl acetate gradient (0–50% ethyl acetate). Yield: 320 mg of 21-acetoxy-11β-hydroxy-6α,16β-dimethyl-17α-propionyloxy-4-pregnene-3,20-dione, mp 139°–140° C.

EXAMPLE 2

(A) Analogously to Example 1(C), 34.4 g of 21-hydroxy-16β-methyl-17α-propionyloxy-4,9(11)-pregnadiene-3,20-dione is reacted with propionic acid anhydride and worked up, yielding 40.0 g of crude 16β-methyl-17α,21-dipropionyloxy-4,9(11)-pregnadiene-3,20-dione, mp 95°–97° C.

(B) 22.0 g of 16β-methyl-17α,21-dipropionyloxy-4,9(11)-pregnadiene-3,20-dione is reacted under the conditions of Example 1(D) with formadehyde dimethylacetal and phosphorus oxychloride, worked up, and purified, thus isolating 13.5 g of 16β-methyl-6-methylene-17α,21-dipropionyloxy-4,9(11)-pregnadiene-3,20-dione, mp 169°–171° C.

(C) Under the conditions of Example 1(E), 13.0 g of 16β-methyl-6-methylene-17α,21-dipropionyloxy-4,9(11)-pregnadiene-3,20-dione is hydrogenated with palladium/active carbon and cyclohexene, worked up, and purified. Yield: 9.8 g of 6α,16β-dimethyl-17α,21-dipropionyloxy-4,9(11)-pregnadiene-3,20-dione, mp 170°–172° C.

(D) Analogously to Example 1(F), 4.0 g of 6α,16β-dimethyl-17α,21-dipropionyloxy-4,9(11)-pregnadiene-3,20-dione is reacted with N-bromosuccinimide and perchloric acid, worked up, and purified, yielding 2.9 g of 9α-bromo-11β-hydroxy-6α,16β-dimethyl-17α,21-dipropionyloxy-4-pregnene-3,20-dione, mp 177°–178° C.

(E) As described in Example 1(G), 1.0 g of 9α-bromo-11β-hydroxy-6α,16β-dimethyl-17α,21-dipropionyloxy-4-pregnene-3,20-dione is debrominated with tributyltin hydride, worked up, and purified. Yield: 710 mg of 11β-hydroxy-6α,16β-dimethyl-17α,21-dipropionyloxy-4-pregnene-3,20-dione, mp 132°–134° C.

EXAMPLE 3

(A) A solution of 1.0 g of 17α,21-(1-ethoxypropylidenedioxy)-16β-methyl-4,9(11)-pregnadiene-3,20-dione in 50 ml of dimethylformamide is stirred, after dropwise addition of 1 ml of trimethylchlorosilane, for 23 hours at a bath temperature of 80° C. After precipitation into ice water and working up the mixture as usual, the crude product is purified on 150 g of silica gel with a methylene chloride-acetone gradient (0–8% acetone). Yield: 680 mg of 21-chloro-16β-methyl-17α-propionyloxy-4,9(11)-pregnadiene-3,20-dione, mp 197°–199° C.

(B) Analogously to Example 1(D), 15.3 g of 21-chloro-16β-methyl-17α-propionyloxy-4,9(11)-pregnadiene-3,20-dione is reacted with formaldehyde dimethylacetal and phosphorus oxychloride, worked up, and purified, thus isolating 9.6 g of 21-chloro-16β-methyl-6-methylene-17α-propionyloxy-4,9(11)-pregnadiene-3,20-dione, mp 199°–200° C.

(C) Under the conditions of Example 1(E), 7.2 g of 21-chloro-16β-methyl-6-methylene-17α-propionyloxy-4,9(11)-pregnadiene-3,20-dione is hydrogenated, worked up, and purified, thus isolating 5.4 g of 21-chloro-6α,16β-dimethyl-17α-propionyloxy-4,9(11)-pregnadiene-3,20-dione, mp 155°–157° C.

(D) As described in Example 1(F), 5.0 g of 21-chloro-6α,16β-dimethyl-17α-propionyloxy-4,9(11)-pregnadiene-3,20-dione is reacted with N-bromosuccinimide and perchloric acid, worked up, and chromatographed. Yield: 5.3 g of 9α-bromo-21-chloro-11β-hydroxy-6α,16β-dimethyl-17α-propionyloxy-4-pregnene-3,20-dione, mp 185°–187° C.

(E) Analogously to Example 1(G), 2.0 g of 9α-bromo-21-chloro-11β-hydroxy-6α,16β-dimethyl-17α-propionyloxy-4-pregnene-3,20-dione is debrominated, worked up, and chromatographed, thus isolating 751 mg of 21-chloro-11β-hydroxy-6α,16β-dimethyl-17α-propionyloxy-4-pregnene-3,20-dione, mp 219°–221° C.

EXAMPLE 4

(A) A solution of 9.5 g of 6α,16β-dimethyl-17α,21-dipropionyloxy-4,9(11)-pregnadiene-3,20-dione in 475 ml of dioxane is refluxed with 9.5 g of dichlorodicyanobenzoquinone for 15 hours. After cooling and filtering off, the filtrate is concentrated to dryness. The crude product is purified on 750 g of silica gel with a hexane-ethyl acetate gradient (0–50% ethyl acetate). Yield of crude product: 5.73 g of 6α,16β-dimethyl-17α,21-dipropionyloxy-1,4,9(11)-pregnatriene-3,20-dione; this product is treated in 20 ml of boiling ethanol dropwise with a solution of 5.73 g of Na₂S₂O₅ in 8 ml of water. After 2 hours, the reaction mixture is treated by distillation so that the volume in the distillation alembic remains preserved by water feed and the bridge thermometer indicates 99° C. The distillation alembic is cooled to +20° C., the mixture is filtered off, the residue is thoroughly washed with water and dissolved in methylene chloride. The organic solution is filtered, after drying, over a silica gel layer and then concentrated. Yield: 4.7 g, mp 188°–190° C.

(B) 3.0 g of 6α,16β-dimethyl-17α,21-dipropionyloxy-1,4,9(11)-pregnatriene-3,20-dione is dissolved in 30 ml of dioxane and, after adding 2.8 g of N-bromosuccinimide, combined dropwise with 15 ml of a 10% perchloric acid. The mixture is agitated for 0.5 hour at room temperature, poured on ice water, and worked up as usual, thus isolating 3.5 g of 9α-bromo-11β-hydroxy-6α,16β-dimethyl-17α,21-dipropionyloxy-1,4-pregnadiene-3,20-dione, mp 186°–187° C.

(C) Under the conditions of Example 1(G), 1.0 g of 9α-bromo-11β-hydroxy-6α,16β-dimethyl-17α,21-dipropionyloxy-1,4-pregnadiene-3,20-dione is debrominated with tributyltin hydride, worked up, and purified, thus obtaining 760 mg of 11β-hydroxy-6α,16β-dimethyl-17α,21-dipropionyloxy-1,4-pregnadiene-3,20-dione, mp 130°–132° C.

EXAMPLE 5

(A) Under the conditions of Example 4(A), 5.2 g of 21-chloro-6α,16β-dimethyl-17α-propionyloxy-4,9(11)-pregnadiene-3,20-dione is dehydrogenated, worked up, and purified, yielding 3.2 g of 21-chloro-6α,16β-dimethyl-17α-propionyloxy-1,4,9(11)-pregnatriene-3,20-dione, mp 199°–200° C.

(B) As described in Example 4(B), 2.2 g of 21-chloro-6α,16β-dimethyl-17α-propionyloxy-1,4,9(11)-pregnatriene-3,20-dione is reacted with 2.0 g of N-bromosuccinimide, worked up, and 2.5 g of 9α-bromo-21-chloro-11β-hydroxy-6α,16β-dimethyl-17α-propionyloxy-1,4-pregnadiene-3,20-dione is thus isolated, mp 180°–182° C.

(C) Analogously to Example 4(C), 700 mg of 9α-bromo-21-chloro-11β-hydroxy-6α,16β-dimethyl-1,4-pregnadiene-3,20-dione is debrominated, worked up, and chromatographed, thus isolating 520 mg of 21-chloro-11β-hydroxy-6α,16β-dimethyl-17α-propionyloxy-1,4-pregnadiene-3,20-dione, mp 205°–206° C.

EXAMPLE 6

(A) Analogously to Example 1(A), 1.0 g of 11β,17α,21-trihydroxy-6α,16β-dimethyl-4-pregnene-3,20-dione is reacted with 1.2 ml of the triethyl ester of orthobutyric acid and worked up, thus isolating 17α,21-(1-ethoxybutylidenedioxy)-11β-hydroxy-6α,16β-dimethyl-4-pregnene-3,20-dione as an oil.

(B) The crude 17α,21-(1-ethoxybutylidenedioxy)-11β-hydroxy-6α,16β-dimethyl-4-pregnene-3,20-dione is hydrolyzed and worked up under the conditions of Example 1(B). The crude product is purified on 100 g of silica gel with a methylene chloride-acetone gradient (0–20% acetone).

Yield: 810 mg of 17α-butyryloxy-11β,21-dihydroxy-6α,16β-dimethyl-4-pregnene-3,20-dione.

EXAMPLE 7

(A) Under the conditions of Example 1(A), 1.0 g of 11β,17α,21-trihydroxy-6α,16β-dimethyl-1,4-pregnadiene-3,20-dione is reacted with the triethyl ester of orthobenzoic acid and worked up, thus isolating 17α,21-(1-ethoxybenzylidenedioxy)-11β-hydroxy-6α,16β-dimethyl-1,4-pregnadiene-3,20-dione as an oil.

(B) Analogously to Example 1(B), the crude 17α,21-(1-ethoxybenzylidenedioxy)-11β-hydroxy-6α,16β-dimethyl-1,4-pregnadiene-3,20-dione is hydrolyzed and worked up. The crude product is purified on 100 g of silica gel with a methylene chloride-acetone gradient (0–8% acetone), thus isolating 680 mg of 17α-benzoyloxy-11β,21-dihydroxy-6α,16β-dimethyl-1,4-pregnadiene-3,20-dione.

EXAMPLE 8

(A) Under the conditions of Example 1(A), 1.0 g of 11β,17α,21-trihydroxy-6α,16β-dimethyl-4-pregnene-3,20-dione is reacted with the triethyl ester of orthoacetic acid and worked up, thus obtaining 17α,21-(1-ethoxyethylidenedioxy)-11β-hydroxy-6α,16β-dimethyl-4-pregnene-3,20-dione as an oil.

(B) The crude 17α,21-(1-ethoxyethylidenedioxy)-11β-hydroxy-6α,16β-dimethyl-4-pregnene-3,20-dione is hydrolyzed and worked up as described in Example 1(B). The crude product is purified on 100 g of silica gel with a methylene chloride-acetone gradient (0–15% acetone). Yield: 840 mg of 17α-acetoxy-11β,21-dihydroxy-6α,16β-dimethyl-4-pregnene-3,20-dione.

EXAMPLE 9

(A) 3.0 g of 21-acetoxy-17α-hydroxy-16β-methyl-4,9(11)-pregnadiene-3,20-dione is reacted analogously to Example 1(D), but with formaldehyde diethylacetal. After a reaction period of one hour, the mixture is worked up and purified. Yield: 1.5 g of 21-acetoxy-17α-hydroxy-16β-methyl-6-methylene-4,9(11)-pregnadiene-3,20-dione, mp 122°–123° C.

(B) Analogously to Example 1(E), 1.4 g of 21-acetoxy-17α-hydroxy-16β-methyl-6-methylene-4,9(11)- pregnadiene-3,20-dione is hydrogenated with cyclohexene and palladium/active carbon, worked up, and purified, thus obtaining 830 mg of 21-acetoxy-17α-hydroxy-6α,16β-dimethyl-4,9(11)-pregnadiene-3,20-dione, mp 197°–199° C.

(C) 5.0 g of 21-acetoxy-17α-hydroxy-6α,16β-dimethyl-4,9(11)-pregnadiene-3,20-dione is dehydrogenated analogously to Example 4(A), worked up, and purified, yielding 3.5 g of 21-acetoxy-17α-hydroxy-6α,16β-dimethyl-1,4,9(11)-pregnatriene-3,20-dione, mp 215°–216° C.

(D) 3.5 g of 21-acetoxy-17α-hydroxy-6α,16β-dimethyl-1,4,9(11)-pregnatriene-3,20-dione is dissolved in 25 ml of anhydrous methylene chloride and 16 ml of formaldehyde dimethylacetal, and combined in incremental portions with a mixture of 5.0 g of kieselguhr W20 and 2.5 g of phosphorus pentoxide. The mixture is stirred for 45 minutes at room temperature, suctioned off, and the residue eluted repeatedly with methylene chloride containing 3–5% of triethylamine. The crude product is purified on 500 g of silica gel with a methylene chloride-acetone gradient (0–10% acetone), thus isolating 2.8 g of 21-acetoxy-17α-methoxymethoxy-6α,16β-dimethyl-1,4,9(11)-pregnatriene-3,20-dione.

(E) Under the conditions of Example 4(B), 2.8 g of 21-acetoxy-17α-methoxymethoxy-6α,16β-dimethyl-1,4,9(11)-pregnatriene-3,20-dione is reacted with N-bromosuccinimide, worked up, and purified. Yield: 2.7 g of 21-acetoxy-9α-bromo-11β-hydroxy-17α-methoxymethoxy-6α,16β-dimethyl-1,4-pregnadiene-3,20-dione.

(F) Analogously to Example 1(G), 2.6 g of 21-acetoxy-9α-bromo-11β-hydroxy-17α-methoxymethoxy-6α,16β-dimethyl-1,4-pregnadiene-3,20-dione is debrominated with tributyltin hydride, worked up, and purified, thus isolating 2.0 g of 21-acetoxy-11β-hydroxy-17α-methoxymethoxy-6α,16β-dimethyl-1,4-pregnadiene-3,20-dione.

EXAMPLE 10

A solution of 700 mg of 21-acetoxy-11β-hydroxy-17α-methoxymethoxy-6α,16β-dimethyl-1,4-pregnadiene-3,20-dione in 8 ml of methanolic 0.2N potassium hydroxide solution is stirred for 40 minutes at 0° C., then neutralized with 10% acetic acid. After precipitation into ice water and working up of the reaction mixture, a crude product is obtained which is purified on 50 g of silica gel with a methylene chloride-acetone gradient (0–15% acetone). Yield: 420 mg of 11β,21-dihydroxy-17α-methoxymethoxy-6α,16β-dimethyl-1,4-pregnadiene-3,20-dione.

EXAMPLE 11

(A) Analogously to Example 9(D), 3.0 g of 21-acetoxy-17α-hydroxy-6α,16β-dimethyl-4,9(11)-pregnadiene-3,20-dione is reacted with formadehyde dimethylacetal, worked up, and purified, thus producing 1.75 g of 21-acetoxy-17α-methoxymethoxy-6α,16β-dimethyl-4,9(11)-pregnadiene-3,20-dione.

(B) As described in Example 1(F), 1.7 g of 21-acetoxy-17α-methoxymethoxy-6α,16β-dimethyl-4,9(11)-pregnadiene-3,20-dione is reacted with N-bromosuccinimide, worked up, and purified. Yield: 810 mg of 21-acetoxy-9α-bromo-11β-hydroxy-17α-methoxymethoxy-6α,16β-dimethyl-4-pregnene-3,20-dione.

(C) Under the conditions of Example 1(G), 800 mg of 21-acetoxy-9α-bromo-11β-hydroxy-17α-methoxymethoxy-6α,16β-dimethyl-4-pregnene-3,20-dione is debrominated with tributyltin hydride, worked up, and purified, thus isolating 415 mg of 21-acetoxy-11β-hydroxy-17α-methoxymethoxy-6α,16β-dimethyl-4-pregnene-3,20-dione.

EXAMPLE 12

Analogously to Example 10, 400 mg of 21-acetoxy-11β-hydroxy-17α-methoxymethoxy-6α,16β-dimethyl-4-pregnene-3,20-dione is saponified with methanolic potassium hydroxide solution, worked up, and purified. Yield: 250 mg of 11β,21-dihydroxy-17α-methoxymethoxy-6α,16β-dimethyl-4-pregnene-3,20-dione.

EXAMPLE 13

(A) A solution of 2.4 g of 9α-bromo-11β-hydroxy-6α,16β-dimethyl-17α,21-dipropionyloxy-1,4-pregnadiene-3,20-dione in 34 ml of acetone is stirred, after adding 3.6 g of potassium carbonate, for 24 hours at room temperature. The potassium carbonate is filtered off, and the filtrate is concentrated under vacuum. The residue is purified on 100 g of silica gel with a hexane-ethyl acetate gradient (0–40% ethyl acetate), thus isolating 1.4 g of 9,11β-epoxy-6α,16β-dimethyl-17α,21-dipropionyloxy-1,4-pregnadiene-3,20-dione, mp 240°–242° C.

(B) A solution, cooled to −40° C., of 3.4 ml of (HF)$_n$/pyridine is agitated, after adding 900 mg of 9,11β-epoxy-6α,16β-dimethyl-17α,21-dipropionyloxy-1,4-pregnadiene-3,20-dione, for 5.75 hours at a temperature of between −20° C. and −10° C. The mixture is poured on an ammoniacal ice water solution, the precipitate is filtered off, and the mixture worked up as usual. The crude product is purified on 100 g of silica gel with a methylene chloride-acetone gradient (0–10% acetone), yielding 540 mg of 9α-fluoro-11β-hydroxy-6α,16β-dimethyl-17α,21-dipropionyloxy-1,4-pregnadiene-3,20-dione.

EXAMPLE 14

(A) Analogously to Example 13(A), 3.0 g of 9α-bromo-11β-hydroxy-6α,16β-dimethyl-17α,21-dipropionyloxy-4-pregnene-3,20-dione is treated with potassium carbonate and worked up, thus isolating 1.95 g of 9,11β-epoxy-6α,16β-dimethyl-17α,21-dipropionyloxy-4-pregnene-3,20-dione, mp 220°–221° C.

(B) Under the conditions of Example 13(B), 1.6 g of 9,11β-epoxy-6α,16β-dimethyl-17α,21-dipropionyloxy-4-pregnene-3,20-dione is reacted with (HF)$_n$/pyridine, worked up, and purified. Yield: 690 mg of 9α-fluoro-11β-hydroxy-6α,16β-dimethyl-17α,21-dipropionyloxy-4-pregnene-3,20-dione, mp 170°–171° C.

EXAMPLE 15

(A) As described in Example 1(A), 1.0 g of 9α-fluoro-11β,17α,21-trihydroxy-6α,16β-dimethyl-4-pregnene-3,20-dione is reacted with the triethyl ester of orthopropionic acid and worked up, thus isolating 17α,21-(1-ethoxypropylidenedioxy)-9α-fluoro-11β-hydroxy-6α,16β-dimethyl-4-pregnene-3,20-dione as an oil.

(B) The crude 17α,21-(1-ethoxypropylidenedioxy)-9α-fluoro-11β-hydroxy-6α,16β-dimethyl-4-pregnene-3,20-dione is reacted under the conditions of Example 1(B), worked up, and purified. Yield: 795 mg of 9α-fluoro-11β,21-dihydroxy-6α,16β-dimethyl-17α-propionyloxy-4-pregnene-3,20-dione.

EXAMPLE 16

Under the conditions of Examples 7(A) and 7(B), 1.0 g of 9α-fluoro-11β,17α,21-trihydroxy-6α,16β-dimethyl-1,4-pregnadiene-3,20-dione is reacted, worked up, and purified, thus isolating 805 mg of 17α-benzoyloxy-9α-fluoro-11β,21-dihydroxy-6α,16β-dimethyl-1,4-pregnadiene-3,20-dione.

EXAMPLE 17

(A) Analogously to Example 13(A), 1.5 g of 21-acetoxy-9α-bromo-11β-hydroxy-6α,16β-dimethyl-17α-propionyloxy-4-pregnene-3,20-dione is reacted with potassium carbonate, worked up, and purified. Yield: 1.05 g of 21-acetoxy-9,11β-epoxy-6α,16β-dimethyl-17α-propionyloxy-4-pregnene-3,20-dione, mp 195°–197° C.

(B) Under the conditions of Example 13(B), 800 mg of 21-acetoxy-9,11β-epoxy-6α,16β-dimethyl-17α-propionyloxy-4pregnene 3,20-dione is reacted with 3 ml of a (HF)$_n$/pyridine solution and worked up, thus obtaining 530 mg of 21-acetoxy-9α-fluoro-11β-hydroxy-6α,16β-dimethyl-17α-propionyloxy-4-pregnene-3,20-dione, mp 167°–16β° C.

EXAMPLE 18

(A) 3.0 g of 9α-bromo-21-chloro-11β-hydroxy-6α,16β-dimethyl-17α-propionyloxy-4-pregnene-3,20-dione is reacted, as described in Example 13(A), with potassium carbonate, worked up, and purified, thus producing 2.1 g of 21-chloro-9,11β-epoxy-6α,16β-dimethyl-17α-propionyloxy-4-pregnene-3,20-dione, mp 201°–202° C.

(B) Under the conditions of Example 13(B), 1.75 g of 21-chloro-9,11β-epoxy-6α,16β-dimethyl-17α-propionyloxy-4-pregnene-3,20-dione is reacted with 6 ml of a (HF)$_n$/pyridine solution, worked up, and purified. Yield: 930 mg of 21-chloro-9α-fluoro-11β-hydroxy-6α,16β-dimethyl-17α-propionyloxy-4-pregnene-3,20-dione, mp 234°–235° C.

EXAMPLE 19

(A) Analogously to Example 13(A), 1.7 g of 9α-bromo-21-chloro-11β-hydroxy-6α,16β-dimethyl-17α-propionyloxy-1,4-pregnadiene-3,20-dione yields, with potassium carbonate, 970 mg of 21-chloro-9,11β-epoxy-6α,16β-dimethyl-17α-propionyloxy-1,4-pregnadiene-3,20-dione, mp 220°–222° C.

(B) As described in Example 13(B), 830 mg of 21-chloro-9,11β-epoxy-6α,16β-dimethyl-17α-propionyloxy-1,4-pregnadiene-3,20-dione is reacted with 3.2 ml of (HF)$_n$/pyridine solution, worked up, and purified, thus obtaining 650 mg of 21-chloro-9α-fluoro-11β-hydroxy-6α,16β-dimethyl-17α-propionyloxy-1,4-pregnadiene-3,20-dione, mp 233°–235° C.

EXAMPLE 20

At 0° C. under argon, 55 ml of a 1.6-molar methyllithium solution is added dropwise to a suspension of 11.1 g of copper(I) iodide in 220 ml of anhydrous tetrahydrofuran. The mixture is further agitated for 15 minutes at 0° C. and the yellowish solution cooled to −30° C. After the dropwise addition of a solution of 8.8 g of 9α-fluoro-11β,17α-dihydroxy-6α,16β-dimethyl-21-valeryloxy-4-pregnene-3,20-dione, the reaction mixture is stirred for 40 minutes at −30° C., then poured on an ice-cold, saturated ammonium chloride solution, and extracted with ethyl acetate. The organic extracts are worked up as usual, and the crude product is purified on 100 g of silica gel with a methylene chloride-acetone gradient (0–20% acetone). Yield: 6.6 g of 9α-fluoro-11β,21-dihydroxy-6α,16β-dimethyl-17α-valeryloxy-4-pregnene-3,20-dione.

EXAMPLE 21

800 mg of 6α,16β-dimethyl-17α,21-dipropionyloxy-1,4,9(11)-pregnatriene-3,20-dione is combined in 8.0 ml of dioxane with 660 mg of N-chlorosuccinimide and, after dropwise addition of 4.0 ml of a 10% perchloric acid solution, agitated for 3 hours at room temperature, then poured on an ice water-sodium chloride solution, and worked up as usual. Yield: 690 mg of 9α-chloro-11β-hydroxy-6α,16β-dimethyl-17α,21-dipropionyloxy-1,4-pregnadiene-3,20-dione, mp 197°–198° C.

EXAMPLE 22

Analogously to Example 21, 800 mg of 21-chloro-6α,16β-dimethyl-17α-propionyloxy-1,4,9(11)-pregnatriene-3,20-dione is reacted with N-chlorosuccinimide, worked up, and purified, thus isolating 620 mg of 9α,21-dichloro-11β-hydroxy-6α,16β-dimethyl-17α-propionyloxy-1,4-pregnadiene-3,20-dione, mp 240°–241° C.

EXAMPLE 23

Under the conditions of Example 21, 1.3 g of 21-chloro-6α,16β-dimethyl-17α-propionyloxy-4,9(11)-pregnadiene-3,20-dione is reacted with N-chlorosuccinimide, worked up, and purified, thus obtaining 590 mg of 9α,21-dichloro-11β-hydroxy-6α,16β-dimethyl-17α-propionyloxy-4-pregnene-3,20-dione, mp 197°–198° C.

EXAMPLE 24

As described in Example 21, 1.0 g of 21-acetoxy-6α,16β-dimethyl-17α-propionyloxy-4,9(11)-pregnadiene-3,20-dione is reacted with N-chlorosuccinimide, worked up, and purified. Yield: 540 mg of 21-acetoxy-9α-chloro-11β-hydroxy-6α,16β-dimethyl-17α-propionyloxy-4-pregnene-3,20-dione, mp 190°–192° C.

EXAMPLE 25

(A) Under the conditions of Example 1(A), 1.0 g of 9α-chloro-11β,17α,21-trihydroxy-6α,16β-dimethyl-1,4-pregnadiene-3,20-dione is reacted with the triethyl ester of orthoacetic acid and worked up, thus isolating 9α-chloro-17α,21-(1-ethoxyethylidenedioxy)-11β-hydroxy-6α,16β-dimethyl-1,4-pregnadiene-3,20-dione as an oil.

(B) The crude 9α-chloro-17α,21-(1-ethoxyethylidenedioxy)-11β-hydroxy-6α,16β-dimethyl-1,4-pregnadiene-3,20-dione is hydrolyzed analogously to Example 1(B), worked up, and purified, thus isolating 860 mg of 17α-acetoxy-9α-chloro-11β,21-dihydroxy-6α,16β-dimethyl-1,4-pregnadiene-3,20-dione.

EXAMPLE 26

(A) Analogously to Example 1(A), 1.0 g of 9α-chloro-11β,17α,21-trihydroxy-6α,16β-dimethyl-1,4-pregnadiene-3,20-dione is reacted with the triethyl ester of orthopropionic acid and worked up, thus isolating 9α-chloro-17α,21-(1-ethoxypropylidenedioxy)-11β-hydroxy-6α,16β-dimethyl-1,4-pregnadiene-3,20-dione as an oil.

(B) Under the conditions of Example 1(B), 9α-chloro-17α,21-(1-ethoxypropylidenedioxy)-11β-hydroxy-6α,16β-dimethyl-1,4-pregnadiene-3,20-dione, as the crude product, is hydrolyzed, worked up, and purified. Yield: 810 mg of 9α-chloro-11β,21-dihydroxy-6α,16β-dimethyl-17α-propionyloxy-1,4-pregnadiene-3,20-dione.

EXAMPLE 27

(A) Under the conditions of Example 1(A), 1.0 g of 9α-chloro-11β,17α,21-trihydroxy-6α,16β-dimethyl-1,4-pregnadiene-3,20-dione is reacted with the triethyl ester of orthobenzoic acid and worked up, thus isolating 9α-chloro-17α,21-(1-ethoxybenzylidenedioxy)-11β-hydroxy-6α,16β-dimethyl-1,4-pregnadiene-3,20-dione as an oil.

(B) The crude 9α-chloro-17α,21-(1-ethoxybenzylidenedioxy)-11β-hydroxy-6α,16β-dimethyl-1,4-pregnadiene-3,20-dione is hydrolyzed, worked up, and purified as described in Example 1(B), thus isolating 710 mg of 17α-benzoyloxy-9α-chloro-11β,21-dihydroxy-6α,16β-dimethyl-1,4-pregnadiene-3,20-dione.

EXAMPLE 28

(A) 1.0 g of 9α-chloro-11β,17α,21-trihydroxy-6α,16β-dimethyl-1,4-pregnadiene-3,20-dione is reacted analogously to Example 1(A) with the triethyl ester of orthobutyric acid and worked up, thus isolating 9α-chloro-17α, 21-(1-ethoxybutylidendedioxy)-11β-hydroxy-6α,16β-dimethyl-1,4-pregnadiene-3,20-dione as an oil.

(B) The crude 9α-chloro-17α,21-(1-ethoxybutylidenedioxy)-11β-hydroxy-6α,16β-dimethyl-1,4-pregnadiene-3,20-dione is, under the conditions of Example 1(B), hydrolyzed, worked up, and purified, yielding 830 mg of 17α-butyryloxy-9α-chloro-11β,21-dihydroxy-6α,16β-dimethyl-1,4-pregnadiene-3,20-dione.

EXAMPLE 29

1.1 g of 17α-butyryloxy-9α-chloro-11β,21-dihydroxy-6α,16β-dimethyl-1,4-pregnadiene-3,20-dione is stirred in 10 ml of pyridine and 5 ml of acetic anhydride for 1.5 hours at room temperature and then poured on ice water. After working up the reaction mixture as usual, the crude product is purified on 100 g of silica gel with a methylene chloride-acetone gradient (0–25% acetone), thus isolating 960 mg of 21-acetoxy-17α-butyryloxy-9α-chloro-11β-hydroxy-6α,16β-dimethyl-1,4-pregnadiene-3,20-dione.

EXAMPLE 30

Under the conditions of Example 29, 1.5 g of 9α-chloro-11β,21-dihydroxy-6α,16β-dimethyl-17α-propionyloxy-1,4-pregnadiene-3,20-dione is reacted with acetic anhydride, worked up, and purified. Yield: 1.4 g of 21-acetoxy-9α-chloro-11β-hydroxy-6α,16β-dimethyl-17α-propionyloxy-1,4-pregnadiene-3,20-dione.

EXAMPLE 31

(A) Analogously to Example 9(D), 4.0 g of 21-acetoxy-17α-hydroxy-6α,16β-dimethyl-1,4,9(11)-pregnatriene-3,20-dione is reacted with 36 ml of formaldehyde diethylacetal, worked up, and purified, thus isolating 2.0 g of 21-acetoxy-17α-ethoxymethoxy-6α,16β-dimethyl-1,4,9-pregnatriene-3,20-dione.

(B) Under the conditions of Example 4(B), 2.0 g of 21-acetoxy-17α-ethoxymethoxy-6α,16β-dimethyl-1,4,9-pregnatriene-3,20-dione is reacted with N-bromosuccinimide and worked up. Yield: 2.2 g of 21-acetoxy-9α-bromo-17α-ethoxymethoxy-11β-hydroxy-6α,16β-dimethyl-1,4-pregnadiene-3,20-dione.

(C) Analogously to Example 1(G), 2.2 g of 21-acetoxy-9α-bromo-17α-ethoxymethoxy-11β-hydroxy-6α,16β-dimethyl-1,4-pregnadiene-3,20-dione is dehalogenated with tributyltin hydride, worked up, and purified, thus obtaining 1.3 g of 21-acetoxy-17α-ethoxymethoxy-11β-hydroxy-6α,16β-dimethyl-1,4-pregnadiene-3,20-dione, mp 137°–139° C.

EXAMPLE 32

A suspension of 0.7 g of 21-acetoxy-17α-ethoxymethoxy-11β-hydroxy-6α,16β-dimethyl-1,4-pregnadiene-3,20-dione in 8 ml of a 0.2N methanolic potassium hydroxide solution is stirred for 30 minutes at 0° C. and thereafter neutralized with 10% strength acetic acid. After performing the usual working-up steps, 470 mg of 17α-ethoxymethoxy-11β,21-dihydroxy-6α,16β-dimethyl-1,4-pregnadiene-3,20-dione is isolated, mp 100°–102° C.

EXAMPLE 33

(A) A solution of 1.0 g of 21-acetoxy-17α-hydroxy-6α,16β-dimethyl-1,4,9-pregnatriene-3,20-dione in 13 ml of diethylene glycol dimethyl ether and 1.5 ml of acetic anhydride is stirred with 1.5 g of N,N-dimethylaminopyridine for 31 hours at 80° C. After precipitation into ice water, the mixture is worked up as usual and chromatographed on 100 g of silica gel with a methylene chloride-acetone gradient, thus isolating 730 mg of 17α,21-diacetoxy-6α,16β-dimethyl-1,4,9-pregnatriene-3,20-dione, mp 134°–136° C.

(B) Analogously to Example 4(B), 500 mg of 17α,21-diacetoxy-6α,16β-dimethyl-1,4,9-pregnatriene-3,20-dione is reacted with N-bromosuccinimide, worked up, and purified. Yield: 565 mg of 17α,21-diacetoxy-9α-bromo-11β-hydroxy-6α,16β-dimethyl-1,4-pregnadiene-3,20-dione, mp 205°–206° C.

(C) As described in Example 1(G), 460 mg of 17α,21-diacetoxy-9α-bromo-11β-hydroxy-6α,16β-dimethyl-1,4-pregnadiene-3,20-dione is debrominated with tributyltin hydride and worked up, thus obtaining 400 mg of 17α,21-diacetoxy-11β-hydroxy-6α,16β-dimethyl-1,4-pregnadiene-3,20-dione, mp 124°–126° C.

EXAMPLE 34

(A) Under the conditions of Example 33(A), 1.0 g of 21-acetoxy-17α-hydroxy-6α,16β-dimethyl-1,4,9-pregnatriene-3,20-dione is treated with propionic anhydride and worked up. After purification, 750 mg of 21-acetoxy-6α,16β-dimethyl-17α-propionyloxy-1,4,9-pregnatriene-3,20-dione is isolated, mp 110°–112° C.

(B) 800 mg of 21-acetoxy-6α,16β-dimethyl-17α-propionyloxy-1,4,9-pregnatriene-3,20-dione is reacted analogously to Example 4(B) with N-bromosuccinimide and worked up. Yield: 850 mg of 21-acetoxy-9α-bromo-11β-hydroxy-6α,16β-dimethyl-17α-propionyloxy-1,4-pregnadiene-3,20-dione, mp 185°–187° C.

(C) The debromination of 800 mg of 21-acetoxy-9α-bromo-11β-hydroxy-6α,16β-dimethyl-17α-propionyloxy-1,4-pregnadiene-3,20-dione is conducted with tributyltin hydride analogously to Example 1(G). After purification, 520 mg of 21-acetoxy-11β-hydroxy-6α,16β-dimethyl-17α-propionyloxy-1,4-pregnadiene-3,20-dione is isolated, mp 115°–117° C.

EXAMPLE 35

(A) As described in Example 33(A), 1.0 g of 21-acetoxy-17α-hydroxy-6α,16β-dimethyl-1,4,9-pregnatriene-3,20-dione is reacted with butyric anhydride, worked up, and purified, thus obtaining 860 mg of 21-acetoxy-17α-butyryloxy-6α,16β-dimethyl-1,4,9-pregnatriene-3,20-dione, mp 88°–90° C.

(B) 800 mg of 21-acetoxy-17α-butyryloxy-6α,16β-dimethyl-1,4,9-pregnatriene-3,20-dione is reacted with N-bromosuccinimide under the conditions of Example 4(B), worked up, and purified. Yield: 830 mg of 21-acetoxy-9α-bromo-17α-butyryloxy-11β-hydroxy-6α,16β-dimethyl-1,4-pregnadiene-3,20-dione, mp 173°–175° C.

(C) Analogously to Example 1(G), 780 mg of 21-acetoxy-9α-bromo-17α-butyryloxy-11β-hydroxy-6α,16β-dimethyl-1,4-pregnadiene-3,20-dione is debrominated with tributyltin hydride, worked up, and purified, thus isolating 610 mg of 21-acetoxy-17α-butyryloxy-11β-hydroxy-6α,16β-dimethyl-1,4-pregnadiene-3,20-dione, mp 106°–108° C.

The preceding examples can be repeated with similar success by substituting the generically or specifically described reactants and/or operating conditons of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 6,16-dimethylcorticoid of the formula

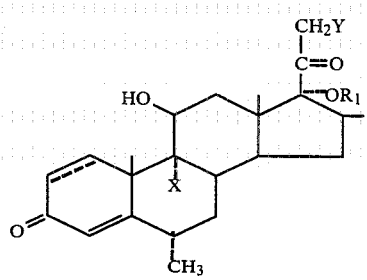

wherein

------- represents a single bond or a double bond;
X is hydrogen, flourine, chlorine, or bromine;
$R_1$ is formyl, alkanoyl or alkoxyalkyl, each of 2–8 carbon atoms, or benzoyl; and
Y is formyl.

2. A compound of claim 1 wherein X is H, F or Cl.

3. A compound of claim 1 wherein any alkanoyl, alkanoyloxy or alkoxyalkyl group is of 1–6 carbon atoms.

4. A compound of claim 1 wherein $R^1$ is ($C_{1-4}$-alkoxy)methyl.

5. A pharmaceutical composition comprising an antiinflammatorily effective amount of a compound of claim 1 and a pharmaceutically acceptable carrier.

6. A pharmaceutical composition of claim 5 adapted for topical application.

7. A pharmaceutical composition of claim 5 adapted for application as an inhalant.

8. A method of treating inflammation in a patient in need of such treatment comprising administering to the patient an anti-inflammatorily effective amount of a compound of claim 1.

9. A steroid of the formula

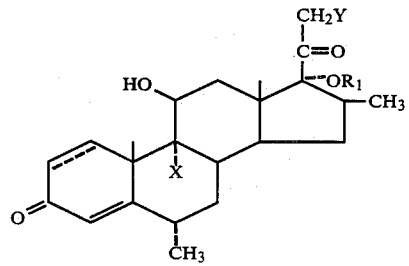

wherein

------- represents a single or double bond;
$R_1$ is formyl, alkanoyl or alkoxyalkyl each of which contains 2–8 carbon atoms, or benzoyl;
Y is chlorine, or formyl;
Z is a carbon-carbon bond or an oxygen atom, and
$R_4$ and $R_5$ together form a methylene group, or
$R_4$ is hydrogen or methyl and
$R_5$ is hydrogen.

10. A compound of claim 9, which is
21-chloro-16β-methyl-17α-propionyloxy-4,9(11)-pregnadiene-3,20-dione,
21-chloro-16β-methyl-6-methylene-17α-propionyloxy-4,9(11)-pregnadiene-3,20-dione,
21-chloro-6α,16β-dimethyl-17α-propionyloxy-4,9(11)-pregnadiene-3,20-dione, or
21-chloro-6α,16β-dimethyl-17α-propionyloxy-1,4,9(11)-pregnatriene-3,20-dione.

11. A compound of a claim 9, which is
21-chloro-9,11β-epoxy-6α,16β-dimethyl-17α-propionyloxy-4-pregnene-3,20-dione, or
21-chloro-9,11β-epoxy-6α,16β-dimethyl-17α-propionyloxy-1,4-pregnadiene-3,20-dione.

12. A 6,16-dimethylcorticoid of the formula wherein

------- represents a single bond or a double bond;
X is hydrogen, flourine, chlorine, or bromine;
$R_1$ is alkoxyalkyl of 2–8 carbon atoms; and
Y is chlorine, hydroxy, formyl, alkanoyloxy of 2–8 carbon atoms, or benzoyloxy.

13. A steroid of the formula

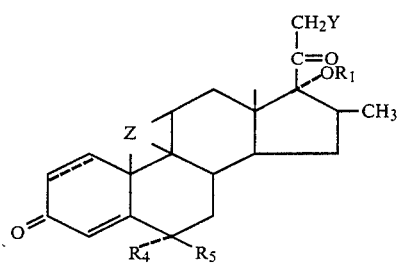

wherein

------ represents a single bond or double bond;

R₁ is alkoxyalkyl of 2–8 carbon atoms;

Y is chlorine, hydroxy, formyl, alkanoyloxy of 2–8 carbon atoms, or benzoyloxy;

Z is a carbon-carbon bond or an oxygen atom, and

R₄ and R₅ together form a methylene group, or

R₄ is hydrogen or methyl and

R₅ is hydrogen.

14. 21-acetoxy-17α-methoxymethoxy-6α,16β-dimethyl-1,4,9(11)-pregnatriene-3,20-dione, or 21-acetoxy-17α-methoxymethoxy-6α,16β-dimethyl-4,9(11)-pregnadiene-3,20-dione, each a compound of claim 13.

15. A pharmaceutical composition comprising an anti-inflammatorily effective amount of a compound of claim 12 and a pharmaceutically acceptable carrier.

16. A method of treating inflammation in a patient in need of such treatment comprising administering to the patient an anti-inflammatorily effective amount of a compound of claim 12.

* * * * *